United States Patent
Schoon et al.

(10) Patent No.: US 12,310,826 B2
(45) Date of Patent: May 27, 2025

(54) LOBE POSITIONER FOR A SEAM BONDER

(71) Applicant: Kimberly-Clark Worldwide, Inc., Neenah, WI (US)

(72) Inventors: Brad W. Schoon, Oshkosh, WI (US); Lars N. Nordang, Neenah, WI (US); Paul D. Mueller, Little Chute, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 18/859,620

(22) PCT Filed: May 24, 2022

(86) PCT No.: PCT/US2022/030695
§ 371 (c)(1),
(2) Date: Oct. 24, 2024

(87) PCT Pub. No.: WO2023/229582
PCT Pub. Date: Nov. 30, 2023

(65) Prior Publication Data
US 2025/0107942 A1    Apr. 3, 2025

(51) Int. Cl.
*B29C 65/08* (2006.01)
*A61F 13/15* (2006.01)
*B29C 65/78* (2006.01)
*B29L 31/48* (2006.01)

(52) U.S. Cl.
CPC ...... *A61F 13/15707* (2013.01); *B29C 65/086* (2013.01); *B29C 65/7832* (2013.01); *B29L 2031/4878* (2013.01)

(58) Field of Classification Search
CPC .......... A61F 13/15707; B29C 65/086; B29C 65/7832; B29L 2013/4878

USPC .......................................... 156/73.4
See application file for complete search history.

(56) References Cited

U.S. PATENT DOCUMENTS

| | | | |
|---|---|---|---|
| 6,197,138 | B1 | 3/2001 | McNichols |
| 7,156,939 | B2 | 1/2007 | Vogt et al. |
| 8,171,972 | B2 | 5/2012 | Eckstein et al. |
| 8,182,627 | B2 | 5/2012 | Eckstein et al. |
| 8,327,904 | B2 | 12/2012 | Yamamoto |

(Continued)

FOREIGN PATENT DOCUMENTS

| | | |
|---|---|---|
| CN | 103690311 A | 4/2014 |
| JP | H0515551 A | 1/1996 |

(Continued)

OTHER PUBLICATIONS

PCT Search Report Corresponding to Application No. PCT/US2022/030695 on Feb. 22, 2023.

(Continued)

*Primary Examiner* — James D Sells
(74) *Attorney, Agent, or Firm* — Dority & Manning, P.A.

(57) ABSTRACT

A seam bonding system includes a drum rotatable about an axis. A seam bonder is mounted to the drum such that the seam bonder is rotatable with the drum about the axis. A horn of the seam bonder is movable along a transverse direction over an anvil of the seam bonder. The seam bonding system also includes features for positioning a lobe of a web material on the drum while the horn of the seam bonder moves along the transverse direction over the anvil of the seam bonder.

16 Claims, 9 Drawing Sheets

(56) References Cited

U.S. PATENT DOCUMENTS

| | | |
|---|---|---|
| 8,596,324 B2 | 12/2013 | Yamamoto |
| 10,342,710 B2 | 7/2019 | Shimada et al. |
| 10,561,539 B2 * | 2/2020 | Schuette ........... B29C 66/81433 |
| 2010/0193135 A1 | 8/2010 | Eckstein et al. |
| 2010/0193138 A1 | 8/2010 | Eckstein et al. |
| 2016/0030252 A1 | 2/2016 | Sayaovong et al. |

FOREIGN PATENT DOCUMENTS

| | | |
|---|---|---|
| KR | 101159213 B1 | 7/2012 |
| KR | 101584629 B1 | 1/2016 |
| KR | 102305977 B1 | 9/2021 |
| KR | 102345264 B1 | 12/2021 |

OTHER PUBLICATIONS

JOA, Slip-Cut Units, 13 Pages, Retrieved from http://www.joa.com/joa-processes/.

* cited by examiner

LOBE POSITIONER FOR A SEAM BONDER

RELATED APPLICATIONS

The present application is the national stage entry of International Patent Application No. PCT/US2022/030695 having a filing date of May 24, 2022, which is incorporated herein in its entirety by reference thereto.

BACKGROUND

Seam bonders join opposing material edges together. For instance, certain disposable undergarments, such as a diaper or incontinence underwear, are constructed with an elastic material with opposing edges joined together at a seam bond. Known seam bonders have drawbacks for some disposable undergarment designs. Moreover, seam bonding certain cuts of elastic material can be difficult due to the elastic properties of the material. Wrinkles, fold-overs, and other defects may arise due to the difficult of holding the elastic material in a desired position.

A positioner for a seam bonder that assists with holding elastic material in a desired position during operation would be useful.

SUMMARY

In general, the present disclosure is directed to a lobe positioner for a side seam bonder. The lobe positioner may include a pair of slides or skis mounted to a side seam bonder horn. The slides may engage and flatten a lobe on a web material to facilitate forming a satisfactory bond at the lobe. Spacer blocks may be mounted on a drum of the side seam bonder. The spacer blocks may apply a force to the web material on the drum. For instance, the spacer blocks may be positioned to allow the slides to push and "pop up" the lobe. A curve on the slides may support the lobe as the bonder horn translates relative to a bonder anvil to form the bond at the lobe. The lobe positioner, e.g., in combination with the spacer blocks, may position and hold the lobe flat while forming the bond at the lobe. For instance, the lobe positioner may be configured to place elastic material in the web into tension in order to orient the lobe, and the lobe positioner may push the lobe into a desired position and orientation as the horn of the side seam bonder rolls across the web to form the bond.

In one example embodiment, a seam bonding system includes a drum rotatable about an axis. A seam bonder is mounted to the drum such that the seam bonder is rotatable with the drum about the axis. A horn of the seam bonder is movable along a transverse direction over an anvil of the seam bonder. A lobe positioner is mounted to the seam bonder such that the lobe positioner is movable along the transverse direction with the horn of the seam bonder. The lobe positioner includes a pair of slides positioned opposite each other about the anvil of the seam bonder. The pair of slides is configured for engaging and positioning a lobe of a web material on the drum when the horn of the seam bonder moves along the transverse direction over the anvil of the seam bonder.

In a first example aspect, the seam bonding system may further include a pair of risers positioned opposite each other about the anvil of the seam bonder. A top of each of the pair of risers may be positioned radially outward of the anvil of the seam bonder on the drum. The pair of risers may include a pair of blocks mounted to the drum. The pair of risers may be integrally formed with the drum. The pair of risers may be positioned on the drum such that pair of slides move between the pair of risers when the seam bonder moves along the transverse direction.

In a second example aspect, each of the pair of slides may defines a rounded lobe engagement tip. A thickness of the rounded lobe engagement tip may be less than a thickness of a middle portion of the slide. Each of the pair of slides may define a curved lift tip opposite the rounded lobe engagement tip.

In a third example aspect, the lobe positioner may further include a bracket and a pair of posts. The pair of posts may be mounted to the bracket. Each of the pair of slides may be mounted to a respective one of the pair of posts at a distal end portion of the respective one of the pair of posts.

In a fourth example aspect, the lobe positioner may further include a pair of springs. Each of the pair of springs may be coupled to a respective one of the pair of slides. The pair of springs may be configured for urging the pair of slides towards the drum.

In a fifth example aspect, a bottom surface of each of the pair slides may face and be positioned generally parallel to an outer surface of the drum.

In a sixth example aspect, the seam bonder may be one of a plurality of seam bonders, and the plurality of seam bonders may be distributed circumferentially around the drum. The lobe positioner may be one of a plurality of lobe positioners, and each of the plurality of lobe positioners may be associated with a respective one of the plurality of seam bonders.

Each of the example aspects recited above may be combined with one or more of the other example aspects recited above in certain embodiments. For instance, all of the six example aspects recited above may be combined with one another in some embodiments. As another example, any combination of two, three, four, or five of the six example aspects recited above may be combined in other embodiments. Thus, the example aspects recited above may be utilized in combination with one another in some example embodiments. Alternatively, the example aspects recited above may be individually implemented in other example embodiments. Accordingly, it will be understood that various example embodiments may be realized utilizing the example aspects recited above.

In another example embodiment, a seam bonding system includes a drum rotatable about an axis. A seam bonder is mounted to the drum such that the seam bonder is rotatable with the drum about the axis. A horn of the seam bonder is movable along a transverse direction over an anvil of the seam bonder. The seam bonding system also includes lobe positioning means for positioning a lobe of a web material on the drum while the horn of the seam bonder moves along the transverse direction over the anvil of the seam bonder.

In another example embodiment, a method for seam bonding includes: rotating a drum with a web disposed on an outer surface of the drum; moving a horn of a seam bonder along a transverse direction over an anvil of the seam bonder; while the horn of the seam bonder moves along the transverse direction over the anvil of the seam bonder, engaging a lobe on the web in order to stretch elastic bands within the lobe; and while the elastic bands within the lobe are stretched, forming a seam bond with the seam bonder.

In a seventh example aspect, the elastic bands within the lobe are in tension while the seam bond is formed by the seam bonder.

These and other features, aspects and advantages of the present disclosure will become better understood with reference to the following description and appended claims.

The accompanying drawings, which are incorporated in and constitute a part of this specification, illustrate embodiments of the disclosure and, together with the description, serve to explain the principles of the disclosure.

BRIEF DESCRIPTION OF THE DRAWINGS

A full and enabling disclosure of the present disclosure, including the best mode thereof, directed to one of ordinary skill in the art, is set forth in the specification, which makes reference to the appended figures.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

As used herein, the terms "includes" and "including" are intended to be inclusive in a manner similar to the term "comprising." Similarly, the term "or" is generally intended to be inclusive (i.e., "A or B" is intended to mean "A or B or both"). Approximating language, as used herein throughout the specification and claims, is applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. For example, the approximating language may refer to being within a ten percent (10%) margin.

Figure 1:
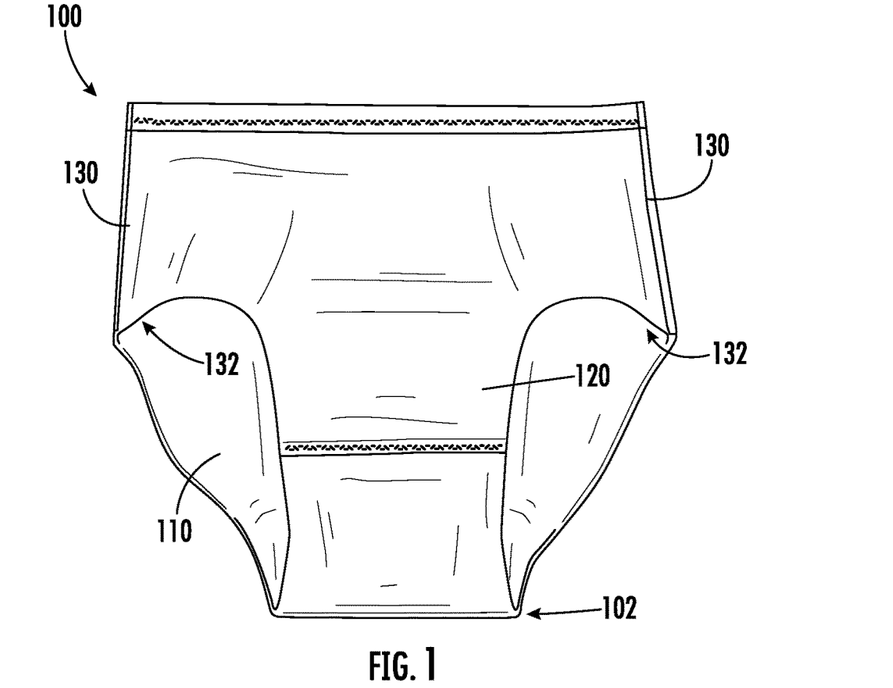
FIG. 1 is a front, elevation view of a disposable undergarment according to an example embodiment of the present disclosure.

FIG. 1 illustrates a disposable undergarment 100 according to an example embodiment of the present disclosure. As shown in FIG. 1, disposable undergarment 100 may include a rear panel 110 and a front panel 120. Rear and front panels 110, 120 of disposable undergarment 100 may be connected at a crotch 102 of disposable undergarment 100. Moreover, rear and front panels 110, 120 of disposable undergarment 100 may be connected at side seams 130. For instance, side seams 130 may be ultrasonically welded to join rear and front panels 110, 120 at side seams 130.

Disposable undergarment 100 may be constructed or with a liquid pervious material, which permits liquids to readily penetrate, or a liquid impervious material, which is resistant to penetration of liquids. For instance, disposable undergarment 100 may be constructed or with natural fibers (such as wood or cotton fibers), synthetic fibers (such as polyester or polypropylene fibers) or from a combination of natural and synthetic fibers or reticulated foams and apertured plastic films. The disposable undergarment 100 may be constructed or with a woven material or a nonwoven material, such as spunbonded material, carded material, extruded material, or the like. Elastic materials may also be incorporated into the disposable undergarment 100. Suitable elastic materials suitable may include elastic threads, yarn rubber, flat rubber, elastic tape, film-type rubber, polyurethane, and, tape-like elastomer, or foam polyurethane or formed elastic scrim.

Figure 2:
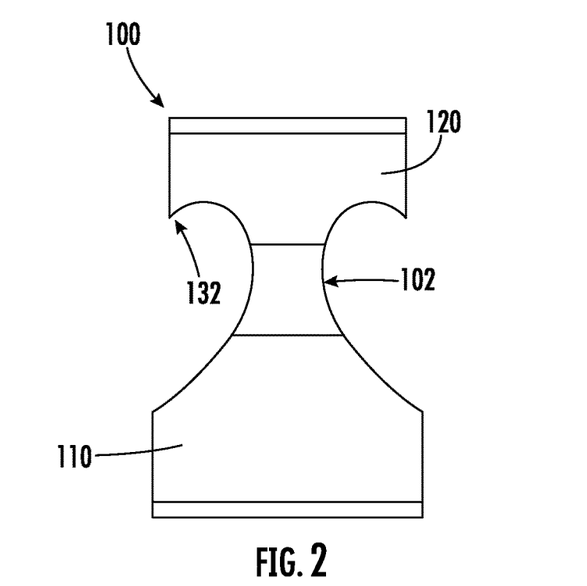
FIG. 2 is a front, plan view of the example disposable undergarment of FIG. 1 in an unbonded arrangement.

FIG. 2 illustrates disposable undergarment 100 prior to forming side seams 130 to join rear and front panels 110, 120 at side seams 130. As an example, the arrangement shown in FIG. 2 may correspond to a material cutout from a die cutting process. As shown in FIG. 2, an upper portion of the front panel 120 may include a lobe 132 after the die cutting process. The lobe 132 may be a flap that contains elastic material therein. In certain example embodiments, two material edges at lobe 132 may meet at an acute angle. For instance, the two material edges at lobe 132 may meet at an angle less than seventy-five degrees) (75°, less than sixty degrees) (60°, about forty-five degrees) (45°, etc. at the free end of the lobe 132.

The elastic material within lobe 132 may cause lobe 132 to pop-up or pop-down during subsequent formation of the side seams 130, e.g., when the material is under tension. As discussed in greater detail below, the present subject matter may assist with flattening or holding lobe 132 in a desired position for formation of side seams 130, e.g., by preventing lobe 132 from popping-up or popping-down and/or subsequently repositioning lobe 132 out popped-up or popped-down position.

Figure 3:
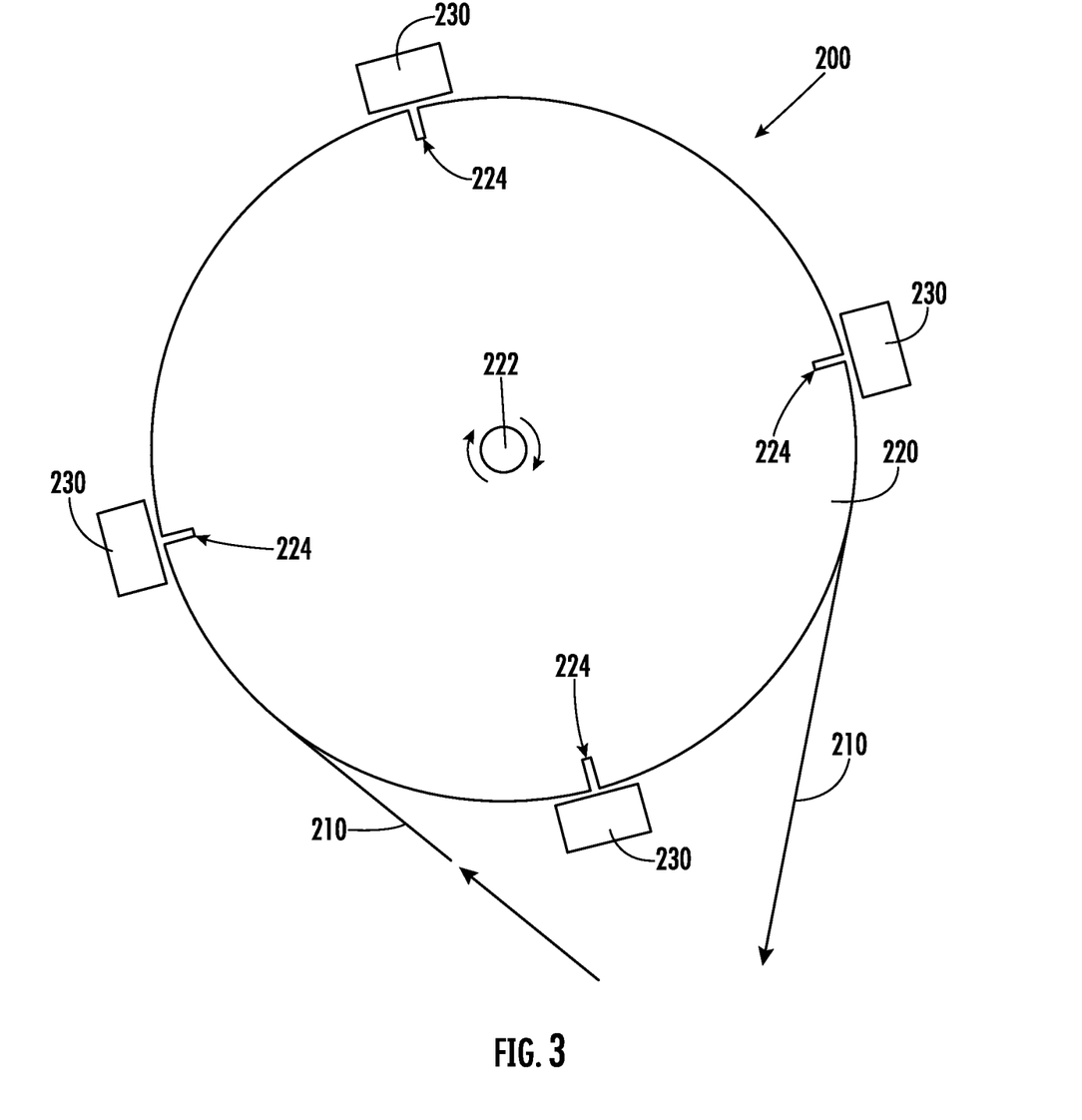
FIG. 3 is a schematic view of a side seam bonder according to an example embodiment of the present disclosure.

FIG. 3 illustrates a seam bonding system 200 according to an example embodiment of the present disclosure. Seam bonding system 200 may be configured for forming side seams 130 of disposable undergarment 100 (FIG. 1). Seam bonding system 200 may be constructed in a similar manner to that describe in U.S. Pat. No. 5,660,657 of Rajala et al., which issued on Aug. 26, 1997, and is incorporated by reference herein for all purposes. As discussed in greater detail below, seam bonding system 200 includes features for positioning lobes 132 of a web material 210 during formation of side seams 130.

Seam bonding system 200 includes a drum 220. Drum 220 is rotatable about an axis on a shaft 222. Web material 210 may be positioned on and move with drum 220 as drum 220 rotates on the axis. Thus, drum 220 may be part of a continuous process for forming side seams 130 of disposable undergarment 100. A plurality of seam bonders 230 are mounted to drum 220. Moreover, seam bonders 230 are rotatable with drum 220 about the axis. Thus, seam bonders 230 rotate with drum 220 during operation of seam bonding system 200. Seam bonders 230 are configured for forming side seams 130 in disposable undergarment 100 from web material 210 on drum 220.

Figure 4:
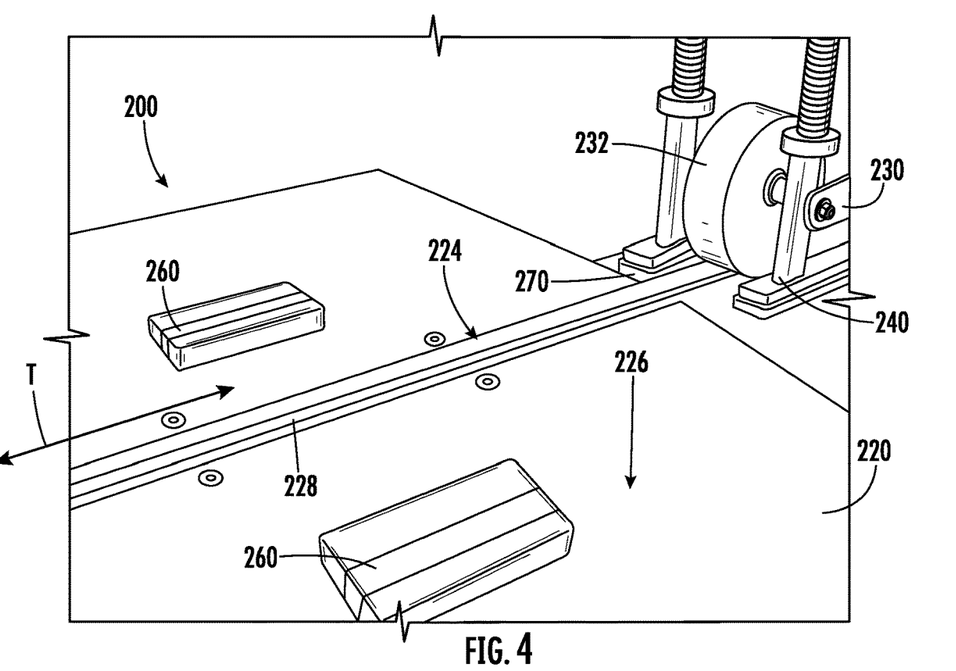
FIG. 4 is a partial elevation view of the example side seam bonder of FIG. 3 with a lobe positioner according to an example embodiment of the present disclosure.

Turning now to FIG. 4, seam bonder 230 may include a horn 232 and an anvil 228. Horn 232 may thus move, e.g., roll, along a transverse direction T over anvil 228. Anvil 228 may be positioned within a slot 224 on drum 220. Thus, e.g., anvil 228 may be recessed within drum 220, e.g., below an outer surface 226 of drum 220 on which web material 210 is disposed. The transverse direction T may be generally parallel to the axis about which drum 220 is rotatable. Horn 232 may be rotatable wheel and may be configured for applying ultrasonic energy, such as ultrasonic acoustic vibrations, to web material 210 on drum 220 during rotation of drum 220 in order to melt the web material 210 at side seams 130 in disposable undergarment 100. For example, horn 232 may roll over anvil 228 on drum 220, and web material 210 may be positioned between anvil 228 and horn 232 on drum 220. Ultrasonic vibration between horn 232 and anvil 228 may melt the web material 210 between anvil 228 and horn 232.

As noted above, seam bonding system 200 includes features for flattening or holding lobe 132 (FIGS. 1 and 2) in a desired position for formation of side seams 130 with seam bonder 230. Moreover, seam bonding system 200 includes a lobe positioner 240 for each of seam bonders 230. Lobe positioner 240 is mounted to seam bonder 230, and lobe positioner 240 is movable along the transverse direction T with horn 232 of seam bonder 230. Thus, e.g., as horn 232 rolls over anvil 228 on drum 220, lobe positioner 240 may translate with seam bonder 230 and position or adjust lobe 132 prior to forming side seams 130.

Figure 5:
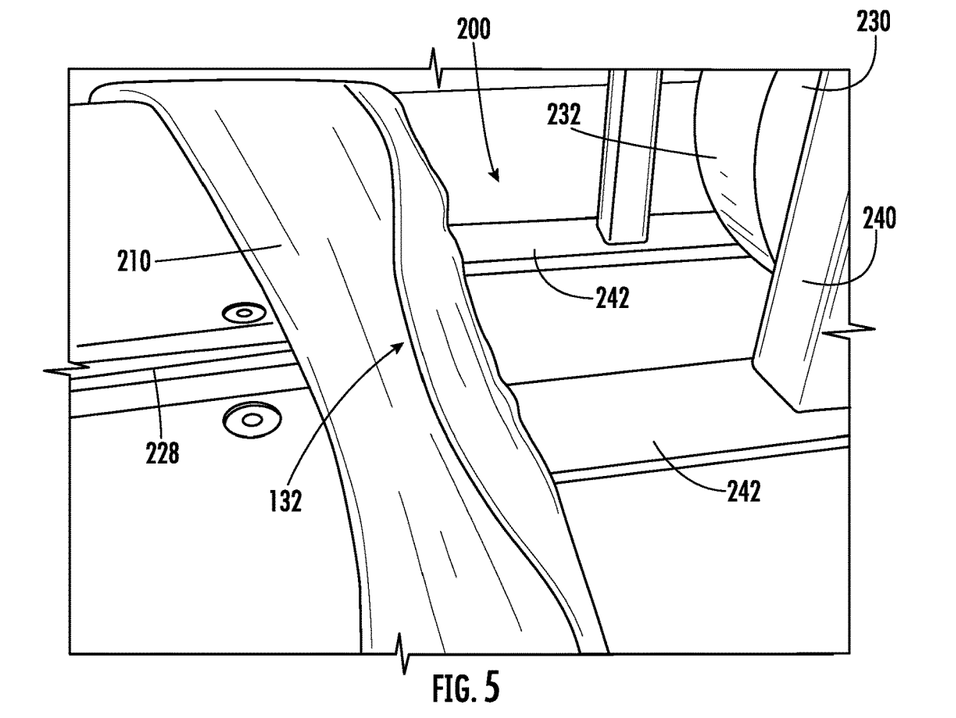
FIG. 5 is a partial elevation view of the example side seam bonder and the example lobe positioner of FIG. 4 during a seam bonding operation.

Lobe positioner 240 may include a pair of slides or skis 242. Slides 242 may be positioned opposite each other about anvil 228. Thus, anvil 228 may be positioned between slides 242 as lobe positioner 240 moves along the transverse direction T with horn 232 of seam bonder 230. Slides 242 may be configured for engaging and positioning lobe 132 of web material 210 on drum 220, as shown in FIG. 5. Moreover, web material 210 on drum 220 may be in tension on outer surface 226 of drum 220, and the free end of lobe 132 may pop-up or pop-down such that lobe 132 is not suitably positioned to form side seams 130. However, prior to forming side seam 130 with seam bonder 230, slides 242 of lobe positioner 240 may contact and move lobe 132 to the proper position for forming side seams 130. Slides 242 may hold lobe 132 in such proper position as horn 232 moves along the transverse direction T over anvil 228 and forms side seam 130. A length of slides 242, e.g., along the transverse direction T, may be no less than seventy-five millimeters (75 mm) and no more than four hundred millimeters (400 mm), no less than one hundred millimeters (100 mm) and no more than three hundred millimeters (300 mm), etc. Such sizing of slides 242 may advantageously assist with allowing slides 242 to hold lobe 132 in the proper position as seam bonder 230 forms side seams 130.

Lobe positioner 240 may also include a pair of risers 260. Risers 260 may be positioned opposite each other about anvil 228 on drum 220. Thus, anvil 228 may be positioned between risers 260 on drum 220. Moreover, risers 260 may be positioned on drum 220 such that slides 242 move between risers 260 when the seam bonder 230 moves along the transverse direction T. Thus, e.g., slides 242 may also be positioned radially closer to outer surface 226 of drum 220 than the tops or distal ends of risers 260.

Risers 260 may extend upwardly from outer surface 226 of drum 220. Thus, a top or distal end of each riser 260 may be positioned radially outward of anvil 228 on drum 220. For instance, the top or distal end of each riser 260 may be positioned radially outward of anvil 228 on drum 220 by no less than six millimeters (6 mm) and no more than seventy-five millimeters (75 mm), no less than twelve millimeters (12 mm) and no more than fifty millimeters (50 mm), or no less than twelve millimeters (12 mm) and no more than twenty-five millimeters (25 mm). Such sizing of risers 260 may advantageously assist with allowing slides 242 to stretch web material 210 at lobe 132 prior to lobe positioner 240 translating with seam bonder 230 along the transverse direction T. The stretching of web material 210 may position lobe 132 for engagement by slides 242, in the manner described in greater detail below.

A width of risers 260, e.g., along the transverse direction T, may be substantially less than a width of drum 220 in certain example embodiments. Moreover, the width of risers 260, e.g., along the transverse direction T, may be no less than seventy-five millimeters (75 mm) and no more than four hundred millimeters (400 mm), no less than one hundred millimeters (100 mm) and no more than three hundred millimeters (300 mm), etc. As a particular example, the width of risers 260, e.g., along the transverse direction T, may be about equal to a width of lobes 132.

As shown in FIG. 4, risers 260 may include a pair of blocks, such as plastic blocks, mounted to drum 220. Thus, e.g., risers 260 may be formed separately from drum 220. In alternative example embodiments, risers 260 may be integrally formed with drum 220. For example, drum 220 may be punched or otherwise machined to form risers 260 from the material of drum 220.

Figure 6:
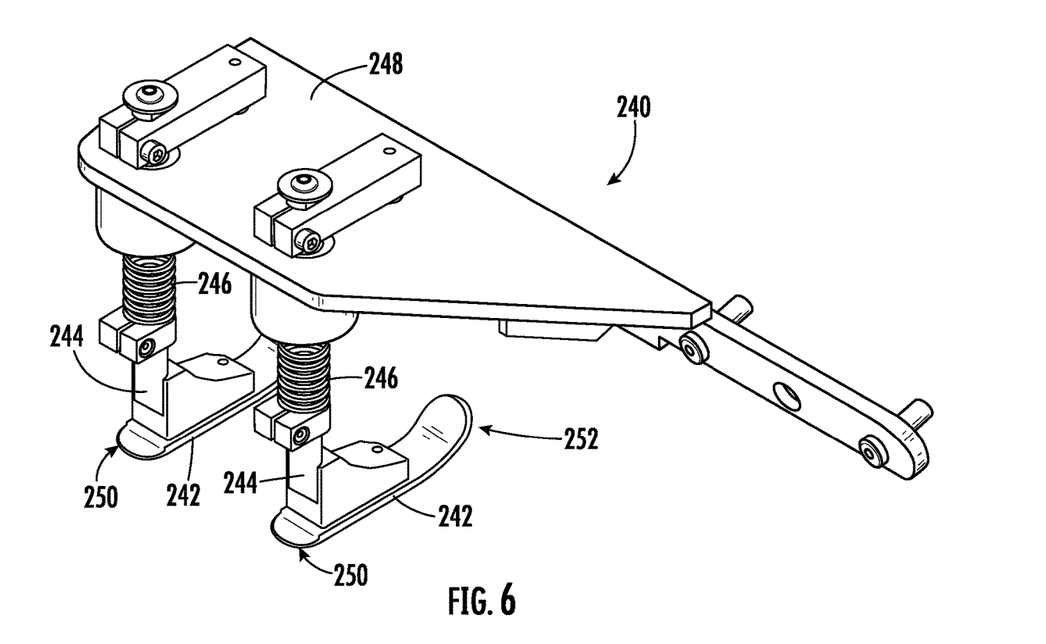
FIG. 6 is an elevation view of the example lobe positioner of FIG. 4.
Figure 7:
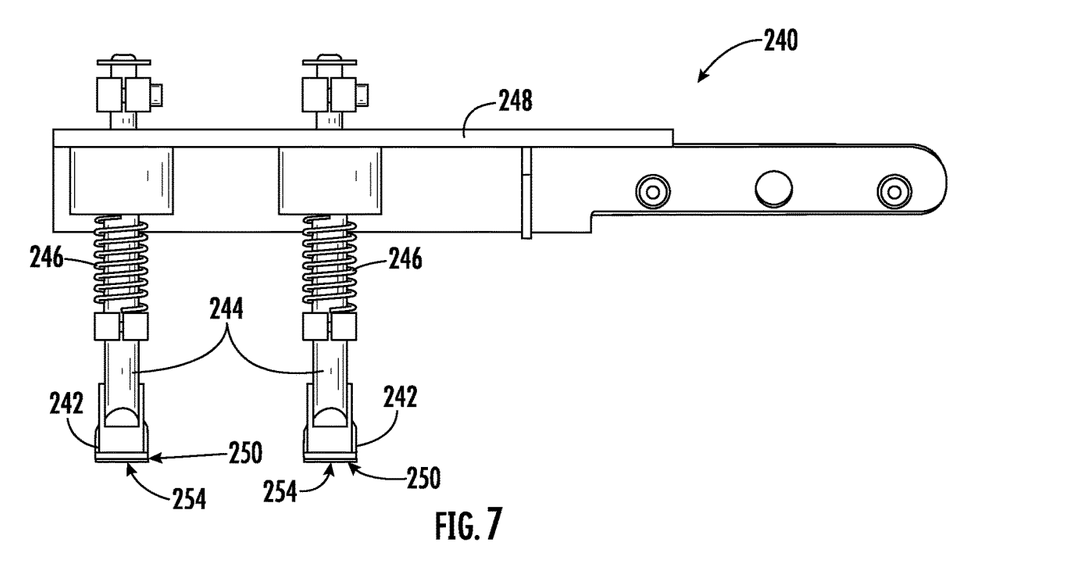
FIG. 7 is a front, elevation view of the example lobe positioner of FIG. 4.

FIGS. 6 and 7, slides 242 may include a rounded lobe engagement tip 250. Rounded lobe engagement tip 250 may face towards lobe 132, e.g., along the transverse direction T. Thus, as lobe positioner 240 moves along the transverse direction T with seam bonder 230, rounded lobe engagement tip 250 may contact and slide under lobe 132, e.g., when lobe 132 is folded over as shown in FIG. 5. As lobe positioner 240 continues to move along the transverse direction T with seam bonder 230 from the position shown in FIG. 5, rounded lobe engagement tip 250 may reposition and flatten lobe 132 to an arrangement suitable for forming side seam 130. Rounded lobe engagement tip 250 may advantageously not pierce or tear web material 210 due to the shape of rounded lobe engagement tip 250. Moreover, a thickness of rounded lobe engagement tip 250 may be less than a thickness of a middle portion of slide 242. For instance, the thickness of rounded lobe engagement tip 250 may taper to a relatively thin edge. Thus, the thickness of slide 242 at rounded lobe engagement tip 250 may be reduced to advantageously facilitate sliding of rounded lobe engagement tip 250 under lobe 132.

Slides 242 may also define a curved lift tip 252, e.g., opposite rounded lobe engagement tip 250. Curved lift tip 252 may face away from lobe 132, e.g., along the transverse direction T. Thus, as lobe positioner 240 moves along the transverse direction T with seam bonder 230 away from lobe 132, curved lift tip 252 may engage a ramp 270 (FIG. 4) at an edge of drum 220. Curved lift tip 252 may slide up ramp 270 to lift lobe positioner 240 radially away from drum 220. Thus, curved lift tip 252 may assist with remove lobe positioner 240 from drum 220, e.g., at the end of seam forming process, in order prevent lobe positioner 240 from obstructing rotation of drum 220 and/or removal of web material 210 from drum 220.

Lobe positioner 240 may also include a bracket 248 and a pair of posts 244. Bracket 248 may be mounted to seam bonder 230 and may assist with coupling lobe positioner 240 to seam bonder 230 such that lobe positioner 240 is translatable with seam bonder 230 along the transverse direction T. Posts 244 may be mounted to bracket 248, and each slide 242 may be mounted to a respective one of posts 244 at a distal end portion of posts 244. Lobe positioner 240 may further include a pair of springs 246. Springs 246 may be coupled to slides 242, and springs 246 may be configured for urging slides 242 towards drum 220.

As shown in FIG. 7, bottom surfaces 254 of slides 242 may be tilted relative to each other. Thus, e.g., bottom surfaces 254 of slides 242 may face and be positioned generally parallel to outer surface 226 of drum 220. Thus, slides 242 may be oriented complementary to the outer surface 226 of drum 220, e.g., which is rounded.

As may be seen from the above, seam bonding system 200 may assist with a forming the side seams 130 of disposable undergarment 100. During use of seam bonding system 200, drum 220 may rotate with web material 210 disposed on outer surface 226 of drum 220. During rotation of drum 220, horn 232 of seam bonder 230 may move along the transverse direction T over anvil 228 on drum 220. While horn 232 moves over anvil 228, lobe positioner 240 may engage lobe 132 on web material 210 in order to stretch elastic bands within lobe 132 and/or web material 210 (e.g., into tension). While the elastic bands within lobe 132 and/or web material 210 are stretched, side seam 130 may be formed with seam bonder 230, e.g., by ultrasonic vibrations melting the web material 210 between horn 232 and anvil 228.

FIGS. 8 through 16 each show a respective lobe positioner according to another example embodiment of the present disclosure. It will be understood that each of the example lobe positioners shown in FIGS. 8 through 16 may be used in or with the seam bonding system 200, e.g., instead or in combination with lobe positioner 240. Moreover, the various lobe positioners shown in FIGS. 8 through 16 may be used in any suitable combination.

Figure 8:
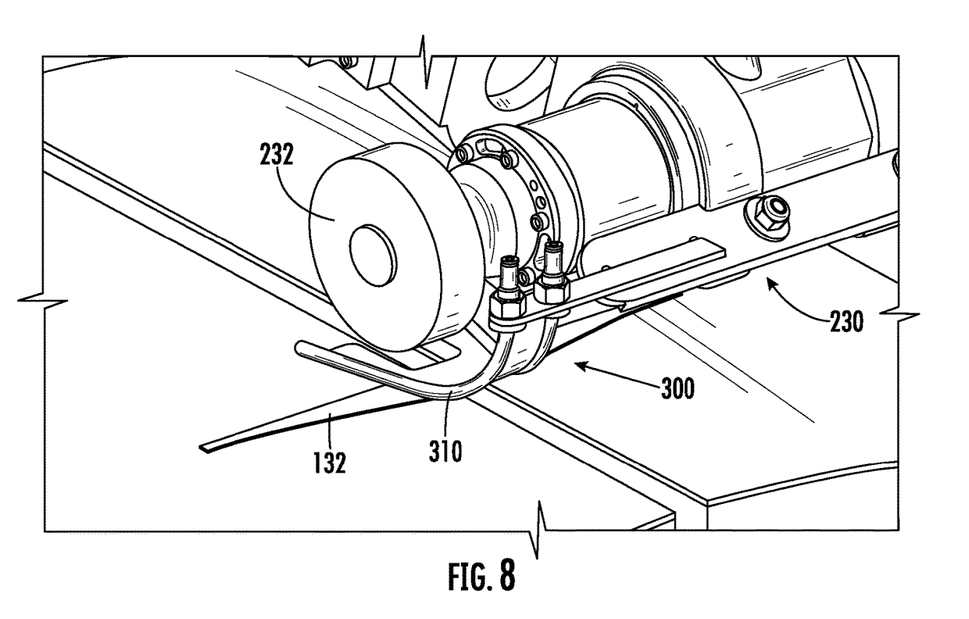
FIGS. 8 through 16 are views lobe positioners according to other example embodiment of the present disclosure.

FIG. 8 shows a lobe positioner 300 according to an example embodiment of the present disclosure. Lobe positioner 300 includes two guide rods with a center plow 310. Guide rods and center plow 310 may slide against and engage lobe 132 in order to position lobe 132 to form side seam 130 with seam bonders 230, e.g., in a similar manner to that described above for lobe positioner 240.

Figure 9:
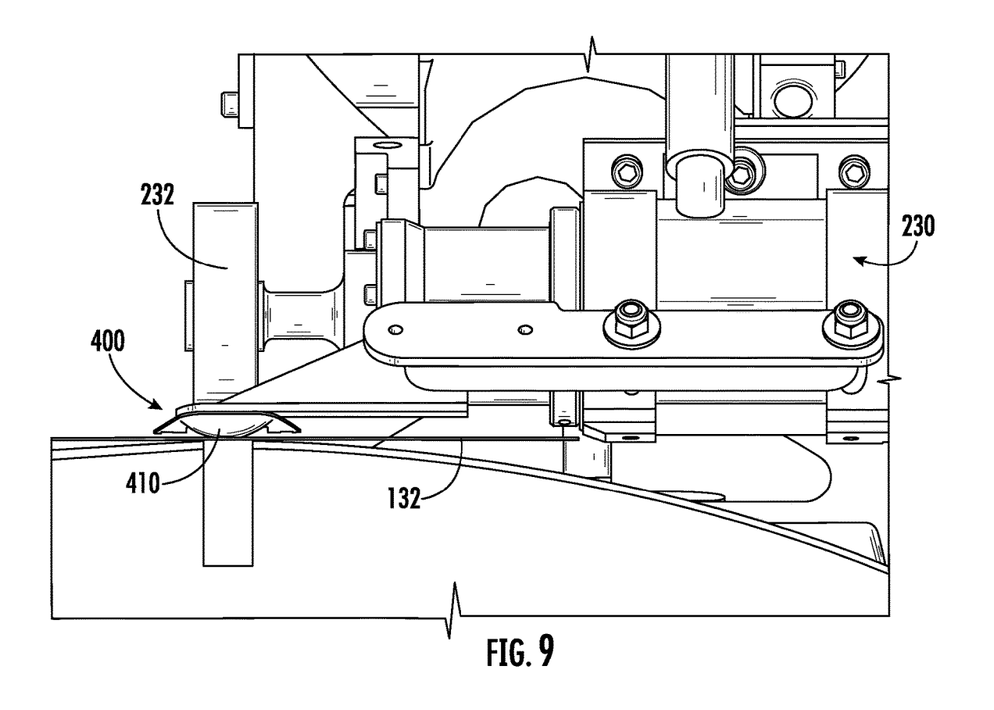

FIG. 9 shows a lobe positioner 400 according to an example embodiment of the present disclosure. Lobe positioner 400 includes a boat 410 with a curved engagement surface. Boat 410 may slide against and engage lobe 132 in order to position lobe 132 to form side seam 130 with seam bonders 230, e.g., in a similar manner to that described above for lobe positioner 240.

Figure 10:
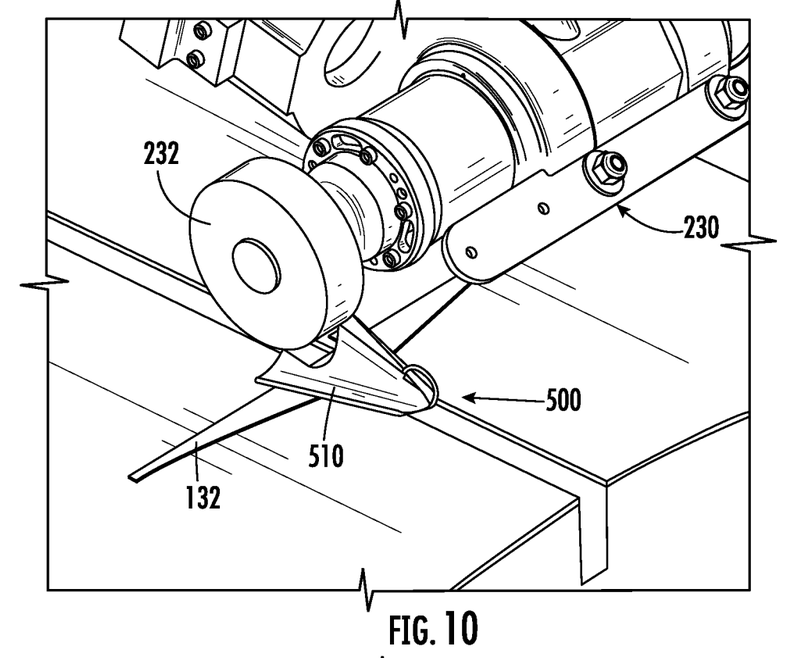

FIG. 10 shows a lobe positioner 500 according to an example embodiment of the present disclosure. Lobe positioner 500 includes a plow 510. Plow 510 may slide against and engage lobe 132 in order to position lobe 132 to form side seam 130 with seam bonders 230, e.g., in a similar manner to that described above for lobe positioner 240.

Figure 11:
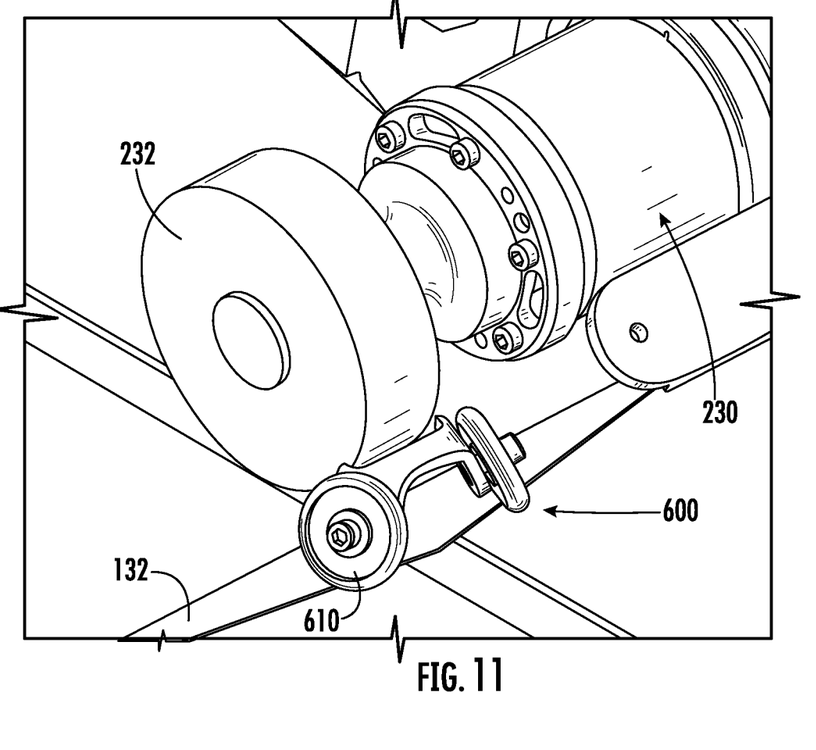

FIG. 11 shows a lobe positioner 600 according to an example embodiment of the present disclosure. Lobe positioner 600 includes a pair of canted wheels 610. Canted wheels 610 may roll on and engage lobe 132 in order to position lobe 132 to form side seam 130 with seam bonders 230, e.g., in a similar manner to that described above for lobe positioner 240.

Figure 12:
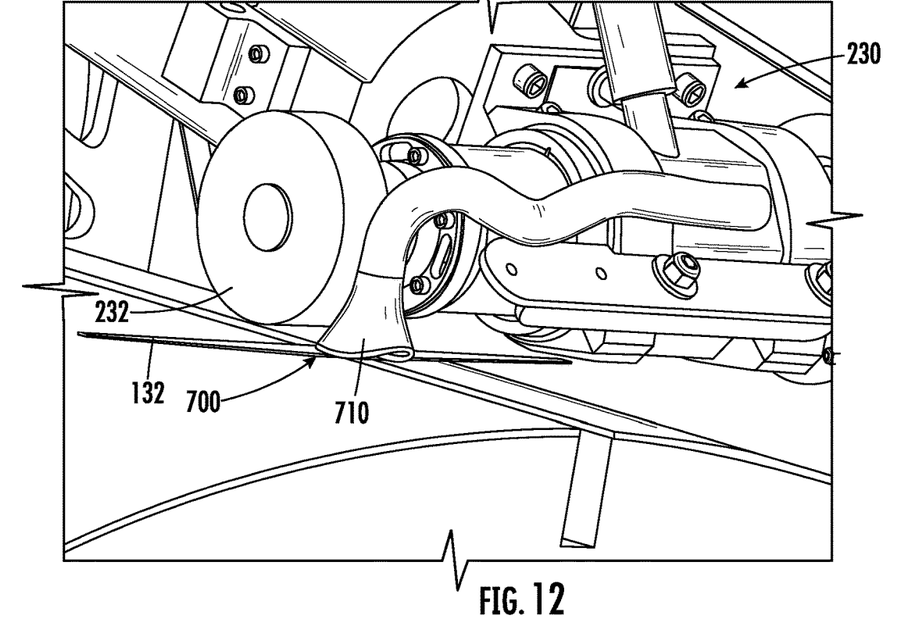

FIG. 12 shows a lobe positioner 700 according to an example embodiment of the present disclosure. Lobe positioner 700 includes a vacuum hose 710. An open end of vacuum hose 710 may face towards lobe 132 and air drawn into vacuum hose 710 may draw lobe 132 into position to form side seam 130 with seam bonders 230, e.g., in a similar manner to that described above for lobe positioner 240.

Figure 13:
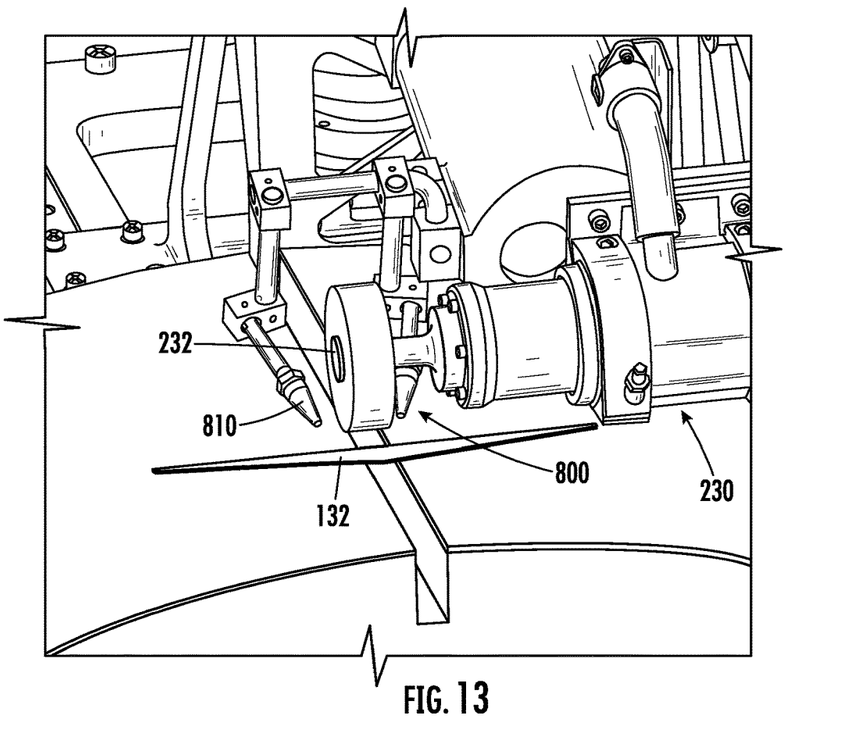

FIG. 13 shows a lobe positioner 800 according to an example embodiment of the present disclosure. Lobe positioner 800 includes one or more air nozzles 810. Air nozzle 810 may be oriented towards lobe 132 and air exiting air nozzle 810 may urge lobe 132 into position to form side seam 130 with seam bonders 230, e.g., in a similar manner to that described above for lobe positioner 240.

Figure 14:
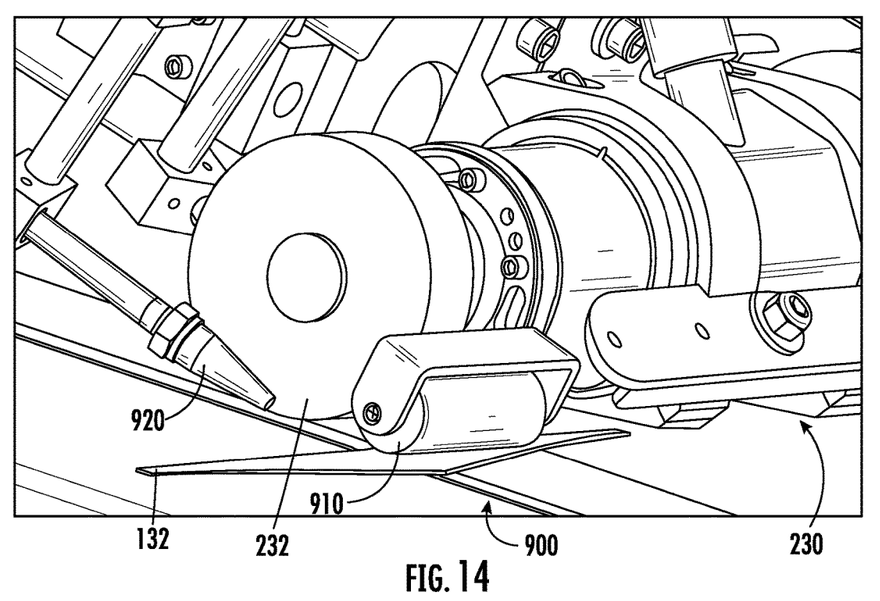

FIG. 14 shows a lobe positioner 900 according to an example embodiment of the present disclosure. Lobe positioner 900 includes a roller brush 910 and an air nozzle 920. Roller brush 910 may roll on and engage lobe 132 and air exiting air nozzle 920 may impact lobe 132 in order to position lobe 132 to form side seam 130 with seam bonders 230, e.g., in a similar manner to that described above for lobe positioner 240.

Figure 15:
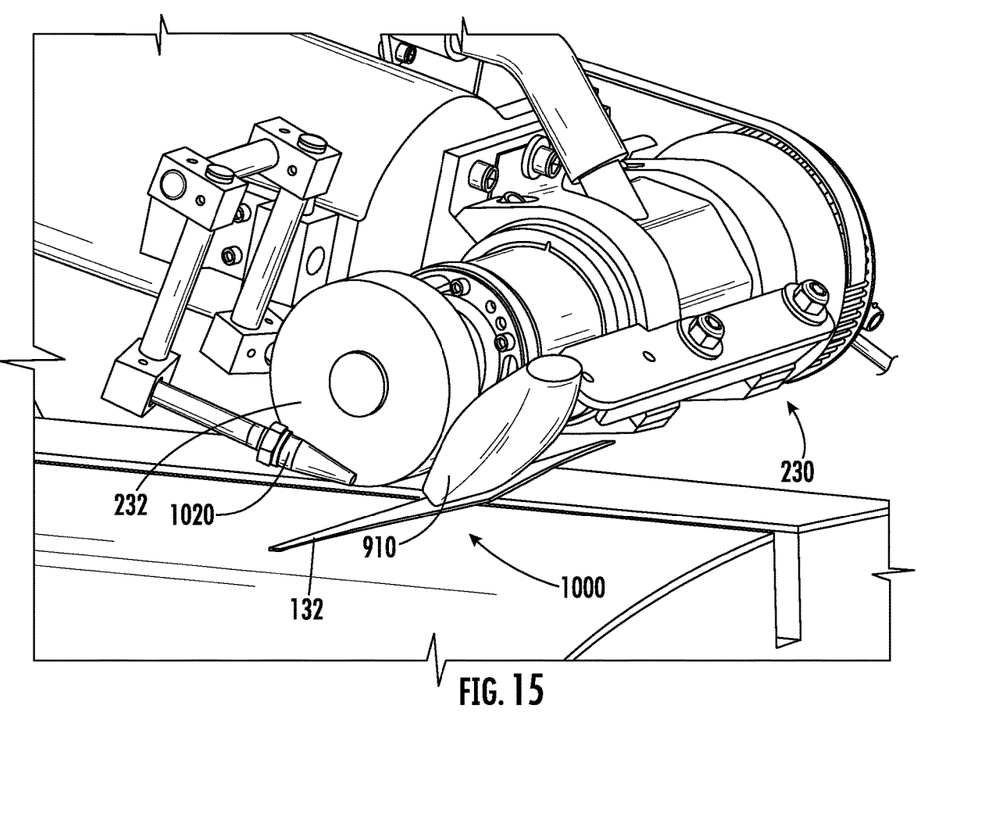

FIG. 15 shows a lobe positioner 1000 according to an example embodiment of the present disclosure. Lobe positioner 1000 includes a sliding brush 1010 and an air nozzle 1020. Sliding brush 910 may slide against and engage lobe 132 and air exiting air nozzle 1020 may impact lobe 132 in order to position lobe 132 to form side seam 130 with seam bonders 230, e.g., in a similar manner to that described above for lobe positioner 240.

Figure 16:
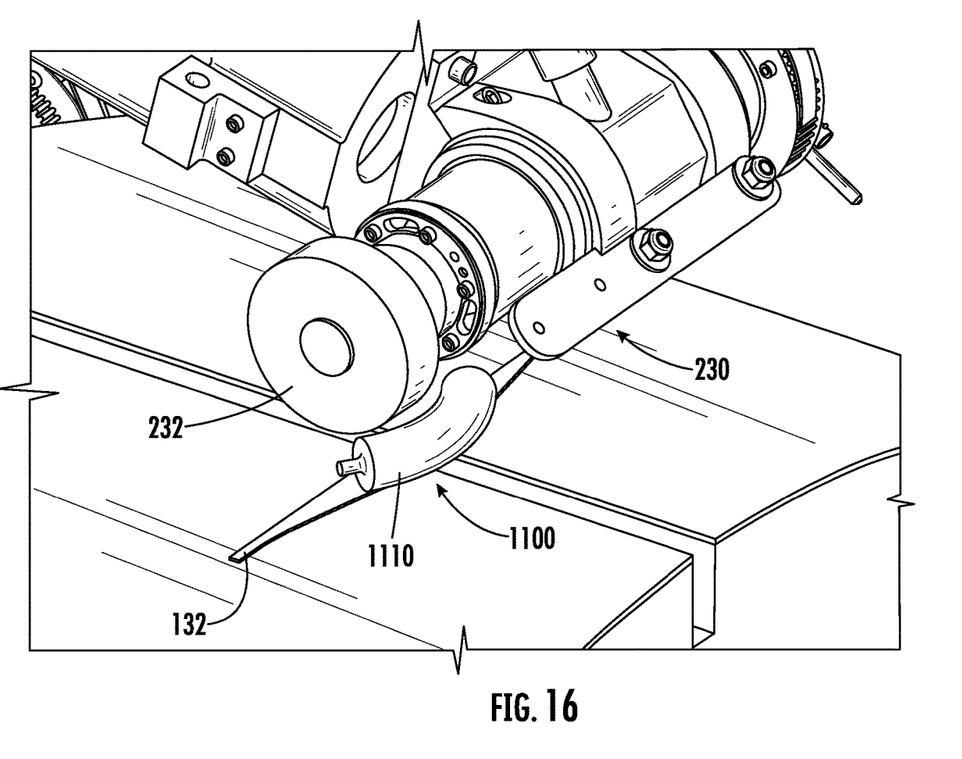

FIG. 16 shows a lobe positioner 1100 according to an example embodiment of the present disclosure. Lobe positioner 1100 includes a bowed roller 1110. Bowed roller 1110 may roll on and engage lobe 132 in order to position lobe 132 to form side seam 130 with seam bonders 230, e.g., in a similar manner to that described above for lobe positioner 240.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

REFERENCE CHARACTERS

100 Disposable undergarment
102 Crotch portion
110 Front panel
120 Rear panel
130 Side seams
132 Lobes
200 Side seam bonder
210 Material web
220 Drum
222 Rotor
224 Slots
226 Outer surface
228 Anvils
230 Seam bonders
232 Horns
240 Lobe positioner
242 Slides
24 Posts
246 Springs
248 Bracket
250 Lobe engagement tips
252 Curved tips
260 Risers

EXAMPLE EMBODIMENTS

First example embodiment: A seam bonding system, includes a drum rotatable about an axis. A seam bonder is mounted to the drum such that the seam bonder is rotatable with the drum about the axis. A horn of the seam bonder is movable along a transverse direction over an anvil of the seam bonder. A lobe positioner is mounted to the seam bonder such that the lobe positioner is movable along the transverse direction with the horn of the seam bonder. The lobe positioner includes a pair of slides positioned opposite each other about the anvil of the seam bonder. The pair of slides is configured for engaging and positioning a lobe of a web material on the drum when the horn of the seam bonder moves along the transverse direction over the anvil of the seam bonder.

Second example embodiment: The seam bonding system of the first example embodiment, further includes a pair of risers positioned opposite each other about the anvil of the seam bonder. A top of each of the pair of risers is positioned radially outward of the anvil of the seam bonder on the drum.

Third example embodiment: The seam bonding system of the second example embodiment, wherein the pair of risers comprise a pair of blocks mounted to the drum.

Fourth example embodiment: The seam bonding system of the second example embodiment, wherein the pair of risers are integrally formed with the drum.

Fifth example embodiment: The seam bonding system of the second example embodiment, wherein the pair of risers positioned on the drum such that the pair of slides move between the pair of risers when the seam bonder moves along the transverse direction.

Sixth example embodiment: The seam bonding system of any one of the first through fifth example embodiments, wherein each of the pair of slides defines a rounded lobe engagement tip.

Seventh example embodiment: The seam bonding system of any one of the first through sixth example embodiments, wherein a thickness of the rounded lobe engagement tip is less than a thickness of a middle portion of the slide.

Eighth example embodiment: The seam bonding system of any one of the first through seventh example embodiments, wherein each of the pair of slides defines a curved lift tip opposite the rounded lobe engagement tip.

Ninth example embodiment: The seam bonding system of any one of the first through eighth example embodiments, wherein the lobe positioner further includes a bracket and a pair of posts. The pair of posts is mounted to the bracket. Each of the pair of slides is mounted to a respective one of the pair of posts at a distal end portion of the respective one of the pair of posts.

Tenth example embodiment: The seam bonding system of any one of the first through nineth example embodiments, wherein the lobe positioner further comprises a pair of springs, each of the pair of springs coupled to a respective one of the pair of slides, the pair of springs configured for urging the pair of slides towards the drum.

Eleventh example embodiment: The seam bonding system of any one of the first through tenth example embodiments, wherein a bottom surface of each of the pair slides faces and is positioned generally parallel to an outer surface of the drum.

Twelfth example embodiment: The seam bonding system of any one of the first through eleventh example embodiments, wherein the seam bonder is one of a plurality of seam bonders, and the plurality of seam bonders are distributed circumferentially around the drum.

Thirteenth example embodiment: The seam bonding system of the twelfth example embodiment, wherein the lobe positioner is one of a plurality of lobe positioners, and each of the plurality of lobe positioners is associated with a respective one of the plurality of seam bonders.

Fourteenth example embodiment: A seam bonding system includes a drum rotatable about an axis. A seam bonder is mounted to the drum such that the seam bonder is rotatable with the drum about the axis. A horn of the seam bonder is movable along a transverse direction over an anvil of the seam bonder. The seam bonding system also includes lobe positioning means for positioning a lobe of a web material on the drum while the horn of the seam bonder moves along the transverse direction over the anvil of the seam bonder.

Fifteenth example embodiment: A method for seam bonding, includes: rotating a drum with a web disposed on an outer surface of the drum; moving a horn of a seam bonder along a transverse direction over an anvil of the seam bonder; while the horn of the seam bonder moves along the transverse direction over the anvil of the seam bonder, engaging a lobe on the web in order to stretch elastic bands within the lobe; and while the elastic bands within the lobe are stretched, forming a seam bond with the seam bonder.

Sixteenth example embodiment: The seam bonding system of the fifteenth example embodiment, wherein the elastic bands within the lobe are in tension while the seam bond is formed by the seam bonder.

What is claimed:

1. A seam bonding system, comprising:
   a drum rotatable about an axis;
   a seam bonder mounted to the drum such that the seam bonder is rotatable with the drum about the axis, a horn of the seam bonder movable along a transverse direction over an anvil of the seam bonder; and
   a lobe positioner mounted to the seam bonder such that the lobe positioner is movable along the transverse direction with the horn of the seam bonder, the lobe positioner comprising a pair of slides positioned opposite each other about the anvil of the seam bonder, the pair of slides configured for engaging and positioning a lobe of a web material on the drum when the horn of the seam bonder moves along the transverse direction over the anvil of the seam bonder.

2. The seam bonding system of claim 1, further comprising a pair of risers positioned opposite each other about the anvil of the seam bonder, a top of each of the pair of risers positioned radially outward of the anvil of the seam bonder on the drum.

3. The seam bonding system of claim 2, wherein the pair of risers comprise a pair of blocks mounted to the drum.

4. The seam bonding system of claim 2, wherein the pair of risers are integrally formed with the drum.

5. The seam bonding system of claim 2, wherein the pair of risers are positioned on the drum such that the pair of slides move between the pair of risers when the seam bonder moves along the transverse direction.

6. The seam bonding system of claim 1, wherein each of the pair of slides defines a rounded lobe engagement tip.

7. The seam bonding system of claim 6, wherein a thickness of the rounded lobe engagement tip is less than a thickness of a middle portion of the slide.

8. The seam bonding system of claim 6, wherein each of the pair of slides defines a curved lift tip opposite the rounded lobe engagement tip.

9. The seam bonding system of claim 1, wherein the lobe positioner further comprises a bracket and a pair of posts, the pair of posts mounted to the bracket, each of the pair of slides mounted to a respective one of the pair of posts at a distal end portion of the respective one of the pair of posts.

10. The seam bonding system of claim 1, wherein the lobe positioner further comprises a pair of springs, each of the pair of springs coupled to a respective one of the pair of slides, the pair of springs configured for urging the pair of slides towards the drum.

11. The seam bonding system of claim 1, wherein a bottom surface of each of the pair slides faces and is positioned generally parallel to an outer surface of the drum.

12. The seam bonding system of claim 1, wherein the seam bonder is one of a plurality of seam bonders, and the plurality of seam bonders are distributed circumferentially around the drum.

13. The seam bonding system of claim 12, wherein the lobe positioner is one of a plurality of lobe positioners, and each of the plurality of lobe positioners is associated with a respective one of the plurality of seam bonders.

14. A seam bonding system, comprising:
- a drum rotatable about an axis;
- a seam bonder mounted to the drum such that the seam bonder is rotatable with the drum about the axis, a horn of the seam bonder movable along a transverse direction over an anvil of the seam bonder; and
- lobe positioning means for positioning a lobe of a web material on the drum while the horn of the seam bonder moves along the transverse direction over the anvil of the seam bonder.

15. A method for seam bonding, comprising:
- rotating a drum with a web disposed on an outer surface of the drum;
- moving a horn of a seam bonder along a transverse direction over an anvil of the seam bonder;
- while the horn of the seam bonder moves along the transverse direction over the anvil of the seam bonder, engaging a lobe on the web in order to stretch elastic bands within the lobe; and
- while the elastic bands within the lobe are stretched, forming a seam bond with the seam bonder.

16. The method of claim 15, wherein the elastic bands within the lobe are in tension while the seam bond is formed by the seam bonder.

* * * * *